United States Patent
Fang et al.

(10) Patent No.: US 9,532,822 B2
(45) Date of Patent: Jan. 3, 2017

(54) PEDICLE SCREW WITH REVERSE SPIRAL CUT AND METHODS THEREOF

(71) Applicant: BLACKSTONE MEDICAL, INC., Lewisville, TX (US)

(72) Inventors: Samuel Fang, Plano, TX (US); Francesco Larosa, Neptune, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 0 days.

(21) Appl. No.: 14/663,651

(22) Filed: Mar. 20, 2015

(65) Prior Publication Data
US 2015/0190186 A1 Jul. 9, 2015

Related U.S. Application Data

(62) Division of application No. 13/802,115, filed on Mar. 13, 2013.

(51) Int. Cl.
*A61B 17/86* (2006.01)
*A61B 17/70* (2006.01)

(52) U.S. Cl.
CPC .......... *A61B 17/863* (2013.01); *A61B 17/864* (2013.01); *A61B 17/8625* (2013.01); *A61B 17/7037* (2013.01)

(58) Field of Classification Search
CPC . A61C 8/0022; A61B 17/863; A61B 17/8625; A61B 17/7037; A61B 17/864
See application file for complete search history.

(56) References Cited

U.S. PATENT DOCUMENTS

| 6,273,722 | B1 | 8/2001 | Phillips |
| 7,922,720 | B2 | 4/2011 | May et al. |
| 7,935,138 | B1 | 5/2011 | Richelsoph |
| 7,993,360 | B2 | 8/2011 | Hacker et al. |
| 2005/0216012 | A1* | 9/2005 | Willmen ............... A61B 17/686 606/323 |
| 2009/0210016 | A1* | 8/2009 | Champagne ......... A61B 17/863 606/309 |
| 2010/0168858 | A1 | 7/2010 | Hardenbrook et al. |

(Continued)

OTHER PUBLICATIONS

Office Action, U.S. Appl. No. 13/802,115, dated Apr. 20, 2015, 24 pages.

(Continued)

*Primary Examiner* — Christopher Beccia
(74) *Attorney, Agent, or Firm* — Baker & McKenzie LLP

(57) ABSTRACT

A pedicle screw with reverse spiral cut that allows for increased loading on a bone and increased osteointegration through automatic and self-managed expansion after the bone screw is inserted into the bone. The bone screw may be a fixation device comprising an elongated body having proximal and distal ends, said elongated body including an outer surface adapted to penetrate and anchor within a bone, and a head affixed to the distal end of the elongated body and adapted to receive a drive component, wherein the outer surface of the elongated body comprises threads extending from the outer surface in a first direction, and further wherein at least a portion of the outer surface of the elongated body comprises a reverse spiral cut into the outer surface in a second direction.

13 Claims, 3 Drawing Sheets

(56) References Cited

U.S. PATENT DOCUMENTS

| | | | | |
|---|---|---|---|---|
| 2010/0190138 | A1* | 7/2010 | Giorno | A61C 8/0022 433/174 |
| 2011/0071579 | A1* | 3/2011 | Reach, Jr. | A61B 17/0401 606/327 |
| 2011/0213367 | A1* | 9/2011 | Tyber | A61B 17/1717 606/62 |
| 2011/0238124 | A1 | 9/2011 | Richelsoph | |
| 2012/0197311 | A1 | 8/2012 | Kirschman | |
| 2013/0072990 | A1 | 3/2013 | Simonson | |
| 2013/0338722 | A1 | 12/2013 | Yalizis | |
| 2014/0039565 | A1* | 2/2014 | Martineau | A61B 17/8625 606/304 |
| 2014/0058460 | A1 | 2/2014 | Reed | |
| 2014/0222011 | A1 | 8/2014 | Keller et al. | |

OTHER PUBLICATIONS

Okuyama, K., et al., "Can Insertional Torque Predict Screw Loosening and Related Failures?: An In Vivo Study of Pedicle Screw Fixation Augmenting Posterior Lumbar Interbody Fusion," SPINE, (1999), vol. 25, No. 7, pp. 858-864.

Jutte, P.C., et al., "Complications of pedicle screws in lumbar and lumbosacrral fusions in 105 consecutive primary operations," Eur Spine J, (2002), vol. 11, pp. 594-598.

Esses, S.I., et al., "Complications Associated with the Technique of Pedicle Screw Fixation: A Selected Survey of ABS Members," SPINE, (1993), vol. 18, No. 15, pp. 2231-2239.

Pihlajamaki, H., et al., "Complications of Transpedicular Lumbosacral Fixation for Non-Traumatic Disorders," The Journal of Bone and Joint Surgery, (Mar. 1997), vol. 79-B, No. 2, pp. 183-189.

Katonis, P., et al., "Complications and Problems Related to Pedicle Screw Fixation of the Spine," Clinical Orthopaedics and Related Research, (Jun. 2003), No. 411, pp. 86-94.

Wittenberg, R.N., et al., "A Biomechanical Study of the Fatigue Characteristics of Thoracolumbar Fixation Implants in a Calf Spine Model," SPINE, (1992), vol. 17, No. 6 Supplement, pp. S121-S128.

Cunningham, B.W., et al., "Static and Cyclical Biomechanical Analysis of Pedicle Screw Spinal Constructs," SPINE, (1993), vol. 18, No. 12, pp. 1677-1688.

Yerby, S.A., et al., "Loading of Pedicle Screws within the Vertebra," Journal of Biomechanics, (1997), vol. 30, No. 9, pp. 951-954.

Chen, S-I., et al., "Biomechanical investigation of pedicle screw-vertebrae complex: a finite element approach using bonded and contact interface conditions," Medical Engineering & Physics, (2003), vol. 25, pp. 275-282.

Chen, C-S., et al., "Failure analysis of broken pedicle screws on spinal instrumentation," Medical Engineering & Physics, (2005), vol. 27, pp. 487-496.

Krag, M.H., et al., "An Internal Fixator for Posterior Application to Short Segments of the Thoracic, Lumbar, or Lumbosacral Spine: Design and Testing," Clinical Orthopedics, (Feb. 1986), No. 203, pp. 75-98.

Lin, J., et al., "Bending Strength and Holding Power of Tibial Locking Screws," Clinical Orthopaedics and Related Research, (Apr. 2001), No. 385, pp. 199-206.

Kwok, A.W.L., et al., "Insertional Torque and Pull-out Strengths of Conical and Cylindrical Pedicle Screws in Cadaveric Bone," SPINE, (1996), vol. 21, No. 21, pp. 2429-2434.

International Search Report and Written Opinion, PCT/US2014/024720, dated Jul. 21, 2014, 9 pages.

\* cited by examiner

PEDICLE SCREW WITH REVERSE SPIRAL CUT AND METHODS THEREOF

CROSS-REFERENCE TO RELATED APPLICATION

This is a divisional application of U.S. application Ser. No. 13/802,115, which was filed on Mar. 13, 2013 and is incorporated herein by reference in its entirety.

TECHNICAL FIELD

The disclosed embodiments relate generally to orthopedic implantable device technology, and more specifically to implantable devices for use in stabilizing the spine, including devices that penetrate the vertebral pedicle, lateral mass, or transverse process and methods for inserting said devices.

BACKGROUND

The bones and connective tissue of an adult human spinal column include more than twenty vertebrae coupled sequentially to one another by a tri-joint complex. The complex includes an anterior disc and two posterior facet joints. The anterior discs of adjacent bones are cushioned by cartilage spacers referred to as intervertebral discs. The vertebrae are each anatomically categorized into one of four classifications: cervical, thoracic, lumbar, and sacral. The cervical portion of the spine, which comprises the top of the spine up to the base of the skull, includes the first seven vertebrae. The intermediate twelve vertebrae are thoracic vertebrae, and connect to the lower spine comprising five lumbar vertebrae. The base of the spine includes the sacral bones (including the coccyx).

The spinal column is highly complex in that it includes over twenty vertebrae coupled to one another for housing and protecting critical elements of the nervous system. These elements of the nervous system include numerous peripheral nerves and circulatory bodies in close proximity to each other. Despite its complexity, the spine is a highly flexible structure, capable of a high degree of curvature and twisting in many different directions.

Spinal pathologies can arise that either limit the range of motion, or threaten the critical elements of the nervous system protected by the spinal column. These pathologies can arise from genetic or developmental irregularities, trauma, chronic stress, tumors and/or disease. A variety of systems are known in the art that provide some degree of immobilization of the spine by implanting artificial assemblies in or onto the spinal column. These assemblies include anterior, posterior, and lateral assemblies. Lateral and anterior assemblies can be coupled to the anterior portion of the spine, typically between vertebral bodies. Posterior spinal fixation systems generally include a pair of rods, which can be aligned along an axis to which the bones are to be disposed, and which are then attached to the spinal column by spinal fixation bone anchors, such as pedicle hooks and/or pedicle screws. Hooks can be coupled to the lamina or attached to transverse processes, while screws can be inserted through pedicles. In order to provide enhanced torsional rigidity, these structures can include cross-connecting devices for coupling the rods together in a direction that is generally transverse with respect to the axis of the rods. These cross-connecting devices can be coupled directly to the rods themselves, or can be attached to the bone anchors. Spinal fixation devices may be surgically implanted in the body to effect a desired relationship between adjacent vertebral bodies. Such devices typically include a rigid stabilizing rod coupled to one or more devices for anchoring the rod to the vertebral bodies. The stabilizing rod must be contoured to accommodate variations in patient anatomy and/or accomplish the desired therapeutic benefits. Since each vertebral body varies in size and shape, a variety of anchoring devices have been developed, including pedicle screws. Pedicle screws have a shape and size appropriate for engaging pedicle bone and may be used to attach external hardware such as rods and plates to the vertebrae.

Traditional pedicle screws are rigid bone screws that, after installation, absorb significant loading in the vertebrate body. Compared with loading the bone itself, loading of the screw weakens the vertebrate bone structure in the vertebrate body and hinders proper load transfer over time due to stress shielding. In some extreme cases, the bone screw may even fracture within the bone, causing pain and discomfort for the patient while also reducing the overall strength of the spinal fixation device.

Although it is undesirable, failure can occur in pedicle screws and such may jeopardize spinal alignment and fixation stability and may lead to severe complications. Loosening of a pedicle screw can occur in a small minority of patients, particularly in osteoporotic spines. It is believed that screw loosening is related to the low pull-off strength of a screw, which measures a screw's purchase power in bone. A screw with a higher pull-off strength generally has a smaller chance of loosening, and thus lead to higher success rate of surgery. In addition, most pedicle screws are rigid and have a very high structural or bending stiffness compared to the surrounding bone. Due to its high structural stiffness, a rigid metal pedicle screw will absorb most of the external loads and unloads the vertebrate bone, a phenomenon called "stress shielding." According to Wolf's law, a bone with less loading will eventually become weaker. This unnatural loading pattern may cause further degradation of the spinal column.

Accordingly, a bone screw that allows for increased loading on the bone in order to promote bone fusion and prevent adjacent level degradation is desired. In addition, a bone screw that allows for increased osteointegration through automatic and self-managed expansion after insertion into the bone is desired.

BRIEF SUMMARY

Disclosed herein is a bone screw comprising a reverse spinal cut that allows for increased loading on a bone and increased osteointegration through automatic and self-managed expansion after the bone screw is inserted into the bone. The bone screw may be a fixation device comprising an elongated body having proximal and distal ends, said elongated body including an outer surface adapted to penetrate and anchor within a bone, and a head affixed to the distal end of the elongated body and adapted to receive a drive component, wherein the outer surface of the elongated body comprises threads extending from the outer surface in a first direction, and further wherein at least a portion of the outer surface of the elongated body comprises a reverse spiral cut into the outer surface in a second direction.

BRIEF DESCRIPTION OF THE DRAWINGS

Embodiments are illustrated by way of example in the accompanying figures, in which like reference numbers indicate similar parts, and in which.

DETAILED DESCRIPTION

Figure 1:
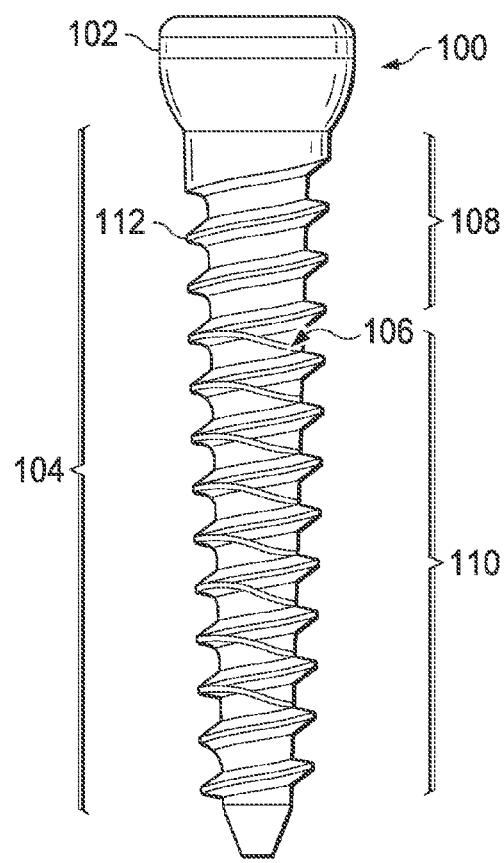
FIG. 1 illustrates a bone screw comprising a reverse spiral cut, in accordance with one embodiment of the present disclosure.

FIG. 1 illustrates a bone screw 100 comprising a reverse spiral cut, in accordance with one embodiment of the present disclosure. The bone screw 100 comprises a head portion 102 at a distal end and an elongated threaded body portion 104 proximal to the head portion 102. The head portion 102 may include a recess (not shown) operable to receive a driving instrument to allow the bone screw 100 to be driven into bone. For example, the recess may be shaped to receive a flat head screwdriver, a Philips head screwdriver, a hex-shaped wrench, or any other shape operable to receive an orthopedic driving instrument. The head may also utilize a shaped outer surface that mates with a corresponding driving instruments.

The threaded body portion 104 of the bone screw 100 may also be referred to as the shank of the bone screw and comprises threads 112. The threads 112 may be left-handed threads or right-handed threads. With right-handed threads, when the bone screw 100 is rotated in a clockwise direction, the bone screw 100 moves away from a viewer when seen from a point of view on an axis through the center of the threaded body portion 104, and when rotated in a counterclockwise direction, the bone screw 100 moves toward a viewer. With left-handed threads, when the bone screw 100 is rotated in a counterclockwise direction, the bone screw 100 moves away from a viewer when seen from a point of view on an axis through the center of the threaded body portion 104, and when rotated in a clockwise direction, the bone screw 100 moves toward a viewer. As shown in FIG. 1, the bone screw 100 comprises a right-handed thread 112.

The threaded body portion 104 of the bone screw 100 further comprises a reverse spiral cut 106. The reverse spiral cut 106 has a cut direction that is opposite the thread direction. As shown in FIG. 1, the reverse spiral cut 106 comprises a left-handed direction. The reverse spiral cut 106 does not penetrate the full diameter of the threaded body portion 104 such that the threaded body portion 104 is continuous and uninterrupted. The location and the length of the reverse spiral cut 106 within the threaded body portion 104 can be adjusted to conform with specific anatomical needs of a patient. For example, and as shown in FIG. 1, a pedicle portion 108 of the threaded body portion 104 proximate to the head portion 102 that interacts with the pedicle may not have any reverse spiral cut, while a vertebrate body portion 110 of the threaded body portion 104 proximal to the pedicle portion 108 and that interacts with the vertebrate body may have a reverse spiral cut 106.

Figure 2:
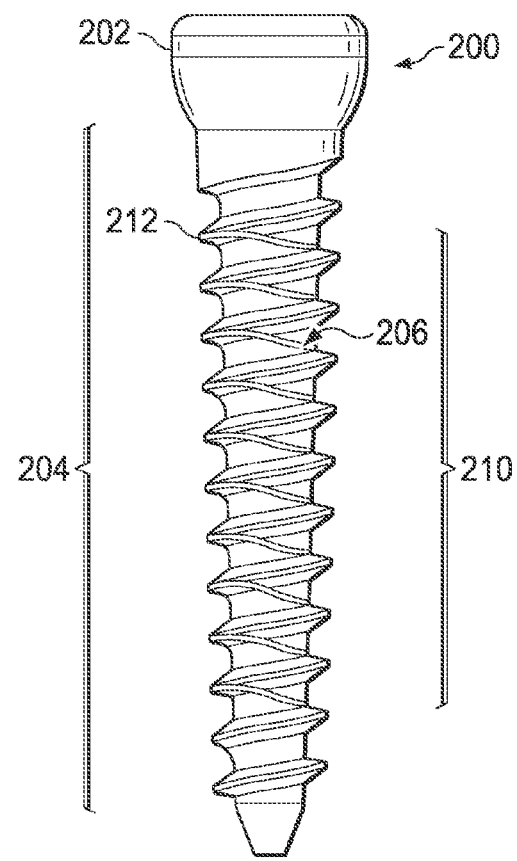
FIG. 2 illustrates a bone screw comprising a reverse spiral cut, in accordance with one embodiment of the present disclosure.

FIG. 2 illustrates a bone screw 200 comprising a reverse spiral cut, in accordance with another embodiment of the present disclosure. The bone screw 200 comprises a head portion 202 at a distal end and a threaded body portion 204 proximal to the head portion 202, threads 212, and reverse spiral cut 206. As shown in FIG. 2, the reverse spiral cut 206 may extend substantially the entire length of the threaded body portion 204. As shown in both FIG. 1 and FIG. 2, the bone screws 100 and 200 may be solid bone screws.

Figure 3:
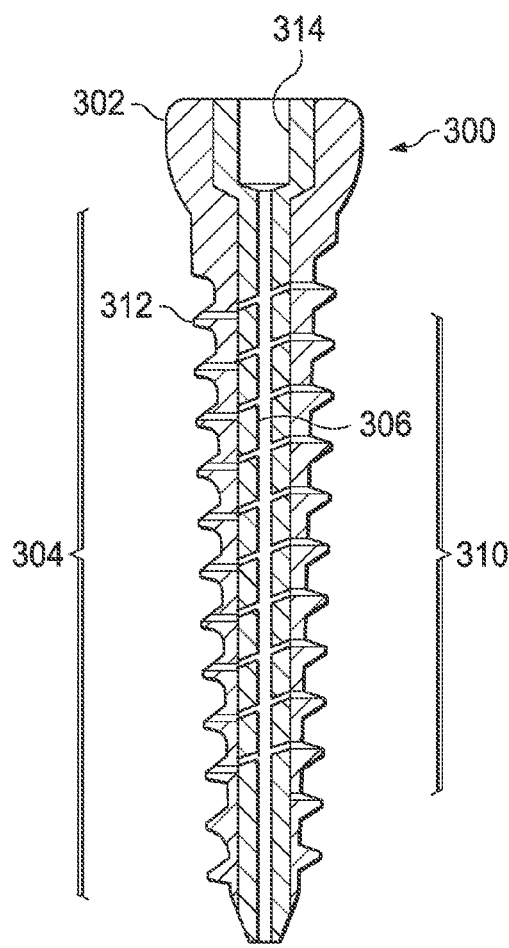
FIG. 3 illustrates a cannulated bone screw comprising a reverse spiral cut with a through hole extending therethrough, in accordance with one embodiment of the present disclosure.

FIG. 3 illustrates a cannulated bone screw 300 comprising a reverse spiral cut, in accordance with another embodiment of the present disclosure. The cannulated bone screw 300 comprises a head portion 302 at a distal end and a threaded body portion 304 proximal to the head portion 302, threads 312, and reverse spiral cut 306. As shown in FIG. 3, the reverse spiral cut 306 may extend substantially the entire length of the threaded body portion 304. The cannulated bone screw 300 may further comprise a hollow shaft 314. With a cannulated bone screw 300, the reverse spiral cut 306 will not penetrate into the hollow shaft 314, such that the threaded body portion 304 remains continuous and uninterrupted.

In operation, and referring now to the bone screws depicted in FIGS. 1-3, the bone screw may be pre-torqued to reduce the major diameter of the threaded body portion of the bone screw and then inserted into the bone at a desired location by applying torque with a driving instrument at the head portion of the bone screw. With a right-handed bone screw, clockwise rotation of the driving instrument drives the bone screw further into the bone, while with a left-handed bone screw, counterclockwise rotation of the driving instrument drives the bone screw further into the bone. The bone screw may be driven directly into the bone at the desired location, or the bone screw may be driven into a pilot hole in the bone at the desired location. If a pilot hole is used, the pilot hole will generally have a smaller diameter than a diameter of the threaded body portion (or screw shank) of the bone screw, allowing the threads of the bone screw to obtain purchase on the bone. After the bone screw is driven into the bone at the desired location, the pre-torque may be released, thereby expanding the major diameter of the threaded body portion of the bone screw.

Figure 4:
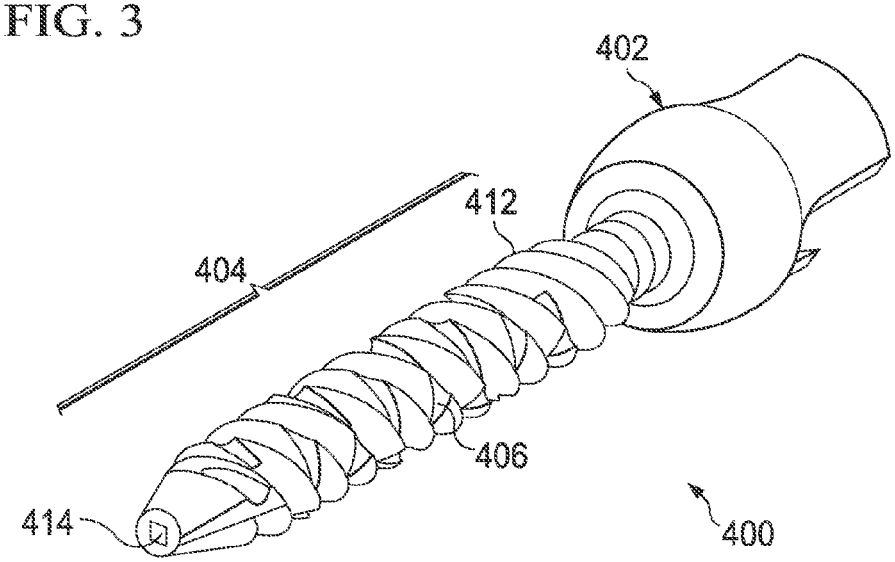
FIG. 4 illustrates a cannulated bone screw comprising a reverse spiral cut with a guide wire retaining feature, in accordance with one embodiment of the present disclosure.
Figure 5:
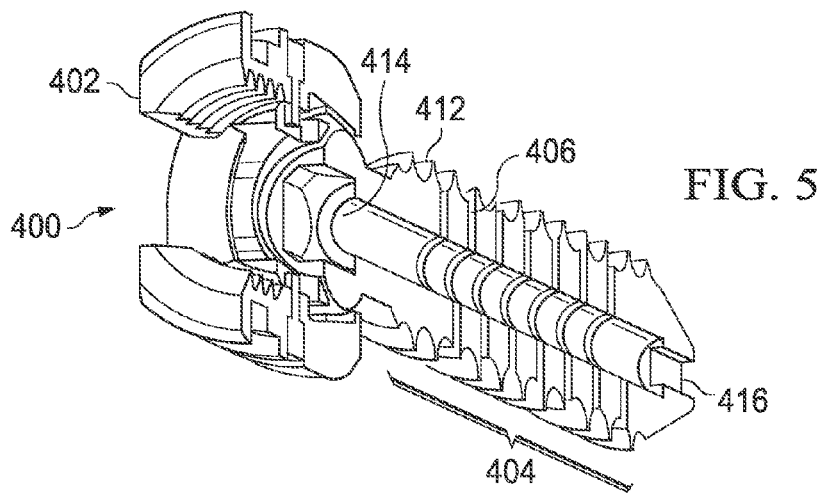
FIG. 5 illustrates a cross sectional view of the cannulated bone screw of FIG. 4, in accordance with one embodiment of the present disclosure.
Figure 6:
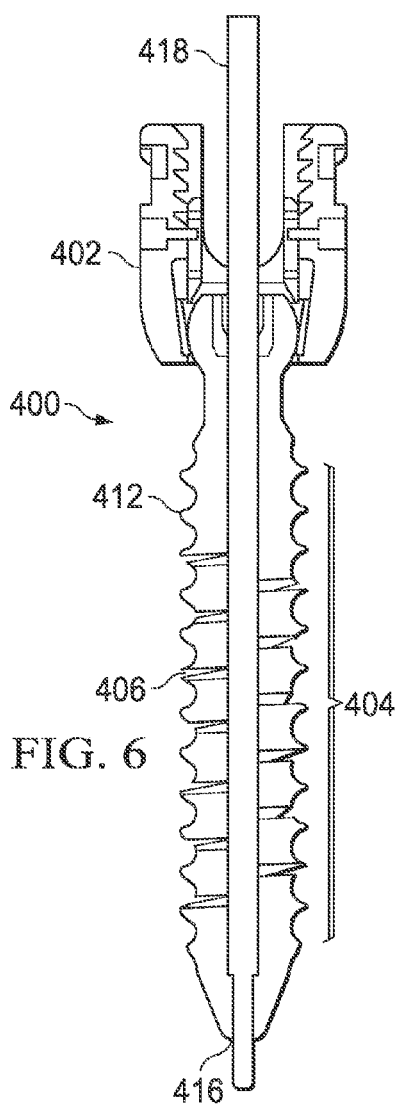
FIG. 6 illustrates a cross sectional view of the cannulated bone screw of FIGS. 4-5 with a guide wire received therethrough, in accordance with one embodiment of the present disclosure.

FIG. 4 illustrates a cannulated bone screw 400 comprising a reverse spiral cut with a guide wire retaining feature 414 in accordance with another embodiment of the present disclosure. FIG. 5 illustrates a cross sectional view of the cannulated bone screw 400 of FIG. 4, in accordance with another embodiment of the present disclosure. FIG. 6 illustrates a cross sectional view of the cannulated bone screw 400 of FIGS. 4-5 with a guide wire 418 received therethrough, in accordance with another embodiment of the present disclosure. The cannulated bone screw 400 comprises a head portion 402 at a distal end, a threaded body portion 404 proximal to the head portion 402, threads 412, and reverse spiral cut 406. As shown in FIGS. 4-6, the reverse spiral cut 406 may extend along substantially the entire length of the threaded body portion 404. The cannulated bone screw 400 may further comprise a hollow shaft 414. With a cannulated bone screw 400, the reverse spiral cut 406 will not penetrate into the hollow shaft 414, such that the threaded body portion 404 remains continuous and uninterrupted.

As shown in FIG. 5, the cannulated bone screw 400 may further comprise a guide wire retaining feature 416 at the proximal end of the screw within the hollow shaft 414. The guide wire retaining feature 416 may be square shaped, although in other embodiments, other shapes such as triangular, pentagonal, hexagonal, etc. may be used. The guide wire retaining feature 416 may be operable to engage with a guide wire (not shown) comprising a tip with the same shape.

As shown in FIG. 6, a guide wire 418 is received within the hollow shaft 414 of the cannulated bone screw 400 and comprises a square tip extending through the square guide wire retaining feature 416 of the cannulated bone screw 400. When the square tip of the guide wire 418 is received through the square guide wire retaining feature 416 of the cannulated bone screw 400, the cannulated bone screw 400 cannot rotate when the guide wire 418 is stationary. However, in addition to the guide wire retaining feature 416 depicted, internal threads or a hexagon cut may be used to prevent rotation of the cannulated bone screw 400 when the guide wire 418 is received therethrough and is stationary.

Figure 7:
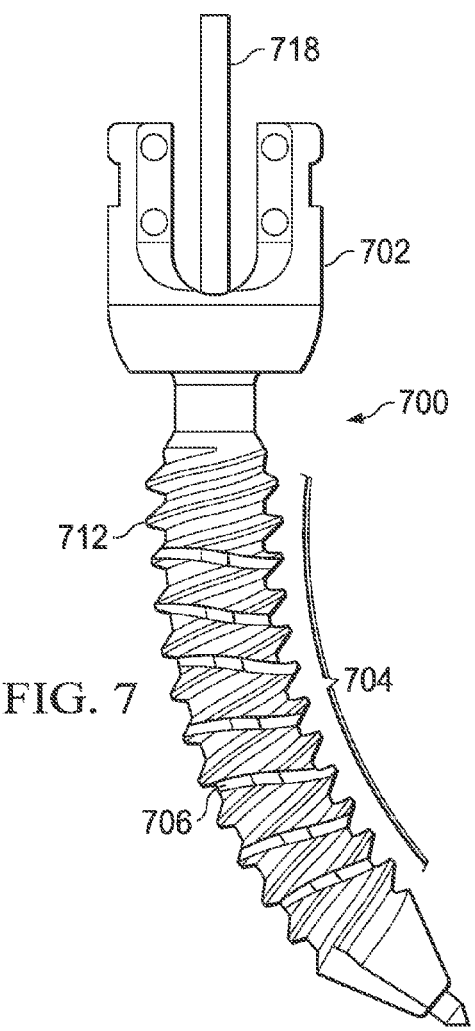
FIG. 7 illustrates a cannulated bone screw comprising a reverse spiral cut with a curved guide wire received therethrough, in accordance with one embodiment of the present disclosure.

FIG. 7 illustrates a cannulated bone screw 700 comprising a reverse spiral cut with a curved guide wire 718 received therethrough, in accordance with another embodiment of the present disclosure. The cannulated bone screw 700 comprises a head portion 702 at a distal end, a threaded body portion 704 proximal to the head portion 702, threads 712, and reverse spiral cut 706. Due to the reverse spiral cut 706, the cannulated bone screw 700 has a low bending stiffness, which allows the threaded body portion 704 to bend easily. As shown in FIG. 7, a curved guide wire 718 is received through the hollow shaft of the cannulated bone screw 700, thereby causing the flexible threaded body portion 704 to bend to match the trajectory of the curved guide wire 718. Compared to commonly used pedicle screws that can only be inserted into bone in a straight orientation, the cannulated bone screw 700 may follow any trajectory defined by a guide wire.

In operation, and referring now to the bone screws depicted in FIGS. 4-7, the bone screw may be pre-torqued to reduce the major diameter of the threaded body portion of the bone screw and then inserted into the bone at a desired location by applying torque with a driving instrument at the head portion of the bone screw. During surgery, a curved pilot hole may be drilled based on a surgeon's preference, the anatomy of the drilled tissue, and the quality of bone that the bone screw is to be inserted into. A flexible guide wire may then be inserted into the curved pilot hole and the bone screw may be inserted into the pilot hole following the guide wire. With a right-handed bone screw, clockwise rotation of the driving instrument drives the bone screw further into the bone, while with a left-handed bone screw, counterclockwise rotation of the driving instrument drives the bone screw further into the bone. The bone screw may be driven directly into the bone at the desired location, or the bone screw may be driven into a pilot hole in the bone at the desired location. If a pilot hole is used, the pilot hole will generally have a smaller diameter than a diameter of the threaded body portion (or screw shank) of the bone screw, allowing the threads of the bone screw to obtain purchase on the bone.

After the guide wire is removed, the curved bone screw provides an anchor point for a spinal rod. By utilizing a curved pilot hole and a flexible guide wire, a curved screw may have an advantageously higher pull-off force compared to a traditional straight screw. In addition, because the bone screw can follow any curved trajectory, the bone screw may be inserted where the bone quality is best suited for a pedicle screw.

Advantageously, during insertion of the bone screw, when torque is applied with a driving instrument at the head portion of the bone screw, the reverse spiral cut of the bone screw allows the diameter of the threaded body portion to be reduced from its natural, resting size when torque is applied with a driving instrument due to a hoop effect caused by the reverse spiral cut. In a resting state, a major diameter for the threaded body portion of the bone screw may be constant. By applying torque at the bone screw head along the direction of the thread reduces the major diameter of the threaded body portion at the spiral cut portion. The major diameter of the spiral cut portion may be reduced due to pre-torque. After insertion of the screw, and when the insertion pre-torque is removed, the major diameter of the threaded body portion will spring back and expand to its natural size. No additional tools or instrumentation is required to expand the major diameter of the bone screw. This automatic and self-managed expansion of the diameter of the threaded body portion will create a pressure on the bone that the bone screw is inserted into, and therefore will increase the purchase power or the pullout strength of the bone screw. The addition of the self-expanding force of the bone screw applied to the surrounding bone, the pull-off strength of the bone screw is greater than that of a traditional bone screw, allowing the bone screw to be used where extra bone purchase power is needed, for example, in a bone with lower bone density, anatomical limitations, or a bone with conditions such as osteopenia or osteoporosis.

In addition, by incorporating a reverse spiral cut, the overall bending stiffness of the current bone screw will be reduced. A traditional bone screw typically comprises a rigid screw body that takes most of the loading itself after insertion into the vertebrae, thereby weakening the vertebrae bone structure and hindering proper load transfers over the course of time due to stress shielding. In extreme conditions, a traditional rigid bone screw may even fracture after being inserted into the vertebrae. Compared to a traditional bone screw without a spiral cut, a bone screw with a spiral cut may have a structural stiffness reduced by up to 85%. Compared to a traditional rigid bone screw, a lower stiffness bone screw design advantageously allows for an increased load to be placed on the bone itself, which helps bone growth and remodeling, facilitates bone fusion, and prevents adjacent level degradation. Most bone screw fractures occur at an internal shank where the internal shank interacts with a vertebrate body. To reduce the likelihood of fracture, the reverse spiral cut may be located in the vertebrate body portion of the threaded body, as shown in FIG. 1.

Furthermore, by incorporating a reverse spinal cut, the bone screw comprises an interconnected space or cavity that the bone is allowed to grow into. This design not only allows bone ongrowth onto the surface of the bone screw, but also bone ingrowth into the internal structure of the bone screw, thereby increasing the fixation of the bone screw and the longevity of the bone screw and the bone.

One or more components of the bone screw with reverse spiral cut disclosed herein may be made from any of the following materials: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, TI-6Al-4V, stainless steel); or (f) any combination thereof.

The dimensions of the screw depends on the anatomy site and the bone quality. For example, for cervical region, the screw major diameter can varies from 2 mm to 4 mm and the length from 6 mm to 30 mm while for lumbar and sacral region, the screw major diameter can varies from 4 mm to 10 mm and length from 25 mm to 100 mm.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention (s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A fixation device comprising:
an elongated body having proximal and distal ends and a hollow shaft extending therebetween, said elongated body including an outer surface adapted to penetrate and anchor within a bone;
a head affixed to the distal end of the elongated body and adapted to mate with a drive component;
wherein the outer surface of the elongated body comprises threads extending from the outer surface in a first direction; and
wherein at least a portion of the outer surface of the elongated body comprises a reverse spiral cut into the outer surface in a second direction; and
wherein the majority of the outer surface of the fixation device is operable to:
be received about a flexible guide wire inserted through the hollow shaft, and
match the pre-defined trajectory of the flexible guide wire.

2. The fixation device of claim 1, wherein the threads extending from the outer surface of the elongated body in the first direction comprises a right-handed thread and wherein the reverse spiral cut into the outer surface of the elongated body in the second direction comprises a left-handed cut.

3. The fixation device of claim 1, wherein the threads extending from the outer surface of the elongated body in the first direction comprises a left-handed thread and wherein the reverse spiral cut into the outer surface of the elongated body in the second direction comprises a right-handed cut.

4. The fixation device of claim 1, wherein a major diameter of the elongated body is operable to be reduced under insertion torque.

5. The fixation device of claim 4, wherein the major diameter of the elongated body is operable to expand after the insertion torque is removed.

6. The fixation device of claim 1, wherein the reverse spiral cut is operable to allow bone ongrowth onto the outer surface of the elongated body and bone ingrowth into an internal structure of the fixation device.

7. The fixation device of claim 1, wherein the fixation device is made from a group consisting of: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, TI-6Al-4V, stainless steel); or (f) any combination thereof.

8. The fixation device of claim 1, wherein the reverse spiral cut does not penetrate a full thickness of the elongated body.

9. The fixation device of claim 1, wherein the reverse spiral cut does not penetrate into the hollow shaft of the elongated body.

10. The fixation device of claim 1, wherein the elongated body further comprises a guide wire retaining feature at the proximal end of the elongated body within the hollow shaft, the guide wire retaining feature being operable to receive a guide wire.

11. The fixation device of claim 10, wherein the guide wire retaining feature is operable to prevent rotation of the elongated body when the guide wire is received through the guide wire retaining feature of the elongated body and the guide wire is stationary.

12. The fixation device of claim 11, wherein the guide wire retaining feature:
comprises one of the following shapes: square, triangular, pentagonal, or hexagonal; and
is operable to engage with a guide wire comprising a tip having the same shape as the guide wire retaining feature.

13. The fixation device of claim 11, wherein,
the elongated body further comprises internal threads or a hexagon cut, and
the guide wire retaining feature is further operable, via the internal threads or the hexagon cut, to prevent rotation of the elongated body when the guide wire is received through the guide wire retaining feature of the elongated body and the guide wire is stationary.

* * * * *